United States Patent [19]

Deniega

[11] Patent Number: 4,590,937
[45] Date of Patent: May 27, 1986

[54] NONMETALLIC SURGICAL CLIP

[75] Inventor: Jose C. Deniega, Brookfield, Conn.

[73] Assignee: American Cyanamid Company, Stamford, Conn.

[21] Appl. No.: 689,342

[22] Filed: Jan. 7, 1985

[51] Int. Cl.$^4$ ............................................. A61B 17/12
[52] U.S. Cl. ...................................... 128/325; 128/346
[58] Field of Search ............... 128/325, 346, 321, 324; 24/255 R, ; 40/23 R

[56] References Cited

U.S. PATENT DOCUMENTS

| | | | |
|---|---|---|---|
| 3,326,217 | 6/1967 | Kerr | 128/325 |
| 3,363,628 | 1/1968 | Wood | 128/325 |
| 3,631,858 | 1/1972 | Ersek | 128/346 |
| 4,390,019 | 6/1983 | Leveen et al. | 128/325 |
| 4,407,285 | 10/1983 | Perlin | 128/325 |
| 4,418,694 | 12/1983 | Beroff et al. | 128/325 |
| 4,458,682 | 7/1984 | Cerwin | 128/346 |
| 4,476,685 | 10/1984 | Failla et al. | 128/325 |

OTHER PUBLICATIONS

Publication Surgery for Sep. 1965 vol. No. 3; p. 20 Advertisement for Hemo-Clip TM by Edward Weck Co.

Primary Examiner—Gene Mancene
Assistant Examiner—Wenceslao J. Contreras
Attorney, Agent, or Firm—Charles F. Costello, Jr.

[57] ABSTRACT

An improved nonmetallic surgical clip having two separate arms joined together at an apex is disclosed. The improvement comprises a weakened portion and a bend in at least one arm. The bend is at the weakened portion. The amount of the bend is such that at least a part of one arm is in an essentially parallel relationship with at least a part of the other arm.

5 Claims, 11 Drawing Figures

NONMETALLIC SURGICAL CLIP

BACKGROUND AND SUMMARY OF THE INVENTION

This invention relates to a improved nonmetallic surgical clip. In a noncrimped configuration, the clip has two separated arms. The improvement is such that at least a part of one arm is in an essentially parallel relationship with at least a part of the other arm.

The improvement comprises a weakened portion and a bend in at least one arm. The bend is at the weakened portion. The weakened portion can be an opening in two (or more) tracks. The tracks are parallel to a length of a clip arm. The weakened portion can also be one or more perforations, indentations or deformations, which can be used either alone or with each other or with the opening in the tracks. It is to be understood that a weakened portion can be on each arm.

When on each arm, the weakened portions are relatively weaker than the cooperating surfaces of the surgical clip but rigid enough to maintain the shape of the clip. This combination of adequate rigidity of the clip in its noncrimped configuration and of the ability of the clip to preselectively begin to crimp at the weakened portions, enables the clip of this invention to ligate a tubular structure in the same manner as a metallic clip. That is, the clip of this invention can be placed around a blood vessel, and, when a force is applied to either or both nonparallel parts of the arms, the tips of the clip touch each other to form a diamond shaped enclosure around the tubular structure.

The advantages of the nonmetallic clip of this invention over the known prior art polymeric ligating clip are many. For example, because the clip forms a diamond shaped enclosure around (that is, it surrounds) the blood vessel, the possibility of the blood vessel extruding out during closing is essentially eliminated. Also, external (to the part of the clip that is in contact with the blood vessel) means for closing the clip can be used with this invention. External closing means eliminate the need to inspect and possibly clean or clear the blood vessel (or other tissue) before the clip cooperating surfaces can be approximated.

An improved nonmetallic surgical clip having two separated arms joined together at an apex has been invented. The improvement comprises a weakened portion and a bend in at least one arm. The bend is at the weakened portion. The amount of the bend is such that at least a part of one arm is in an essentially parallel relationship with at least a part of the other arm.

In one embodiment, the nonmetallic material is a synthetic bioadsorbable polymer. In a specific embodiment, the polymer has a glycolic acid ester linkage.

In another embodiment, at least a portion of the cooperating surfaces of the arms are essentially flat. In a further embodiment, at least a portion of the cooperating surfaces of the arms are serrated.

Alternatively, the improvement to each arm comprises a weakened portion and a bend. The bend is at the weakened portion. Part of each arm is in an essentially parallel relationship whereby a force applied to either or both nonparallel parts of each arm causes the clip to form a diamond shaped enclosure.

In one embodiment, the nonmetallic material is a synthetic bioabsorbable polymer. In a specific embodiment, the polymer has a glycolic acid ester linkage. In a more specific embodiment, the polymer is a homopolymer.

In another embodiment, at least a portion of the cooperating surfaces of the arms are essentially flat. In a further embodiment, the force applied to either or both non-parallel parts of each arm is by a means for approximating the cooperating surfaces of the arms.

A nonmetallic surgical clip has also been invented. The clip has two separate parts. The first part comprises two arms joined together at an apex, a weakened portion and a bend in at least one arm. The bend is at the weakened portion. The amount of the bend is such that at least a part of one arm is in an essentially parallel relationship with at least a part of the other arm. The second part comprises means for approximating the cooperating surfaces of the arms.

In one embodiment, the nonmetallic material is a synthetic bioabsorbable polymer having a glycolic acid ester linkage. In a specific embodiment, the first part is a copolymer containing glycolic acid ester and trimethylene carbonate linkages, and the second part is a homopolymer of glycolic acid.

In another embodiment, the arms are in an essentially symmetrical relationship.

In a further embodiment, the apex of the first part is essentially contiguous with a portion of the second part. In a specific embodiment, the approximating means is a U-shaped member.

In a final embodiment, the first part contains a protrusion. The protrusion is adjacent to the apex and is opposite the proximal ends of the arms. In a specific embodiment, the approximating means is a U-shaped member. In a more specific embodiment, the distal end of the U-shaped member is contacting said protrusion.

DESCRIPTION OF THE INVENTION

Figure 1:
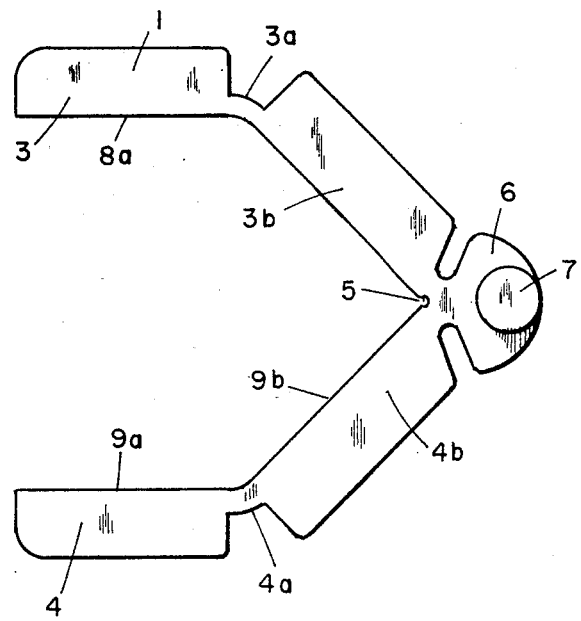
FIGS. 1 to 4 are side, top, back and front views, respectively, of a surgical clip of this invention.
Figure 3:
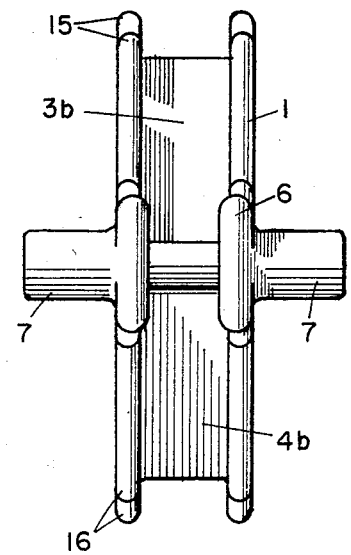

FIGS. 1 to 4 and 5 to 7 describe a surgical ligating clip having two separate parts 1 and 2, respectively.

Referring to FIGS. 1 to 4, part 1 comprises two essentially parallel arms 3 and 4. Preferably, the two arms 3 and 4 are essentially symmetrical. The two arms 3 and 4 are joined at their proximal ends to two nonparallel members 3b and 4b, respectively. The proximal ends of the two nonparallel members 3b and 4b are joined together at an apex 5.

Figure 9:
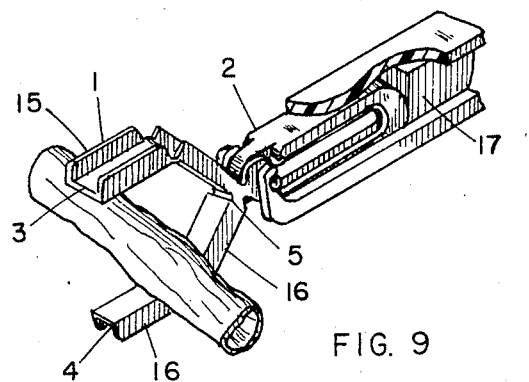
FIG. 9 is a perspective view showing a clip of FIG. 1 as a first part, in an open configuration, and the U-shaped member of FIG. 5 as a second part, both parts being contained by a mechanical applicator.

Preferably, part 1 also contains a protrusion 6. More preferably, the protrusion 6 is adjacent the apex 5. The protrusion 6 provides means for holding the part 1 in a contiguous relationship with the distal end of the part 2, as shown e.g. in FIG. 9. Referring to FIG. 9, the proximal ends of tracks 15 and 16 of part 1 can also be essentially contiguous with the distal end of part 2.

The arms 3 and 4 and the nonparallel members 3b and 4b are approximated by sliding the legs 10 and 11 of part 2 between the respective tracks 15 and 16 of part 1.

Referring to FIGS. 1 to 4 and 8 to 11, the arms 3 and 4 and the respective nonparallel members 3b and 4b are preferably in an essentially symmetrical relationship. Referring specifically to FIG. 1, the cooperating surfaces 8a and 9a of arms 3 and 4 and/or 8b and 9b of members 3b and 4b can be flat. In another embodiment, either one or both of the cooperating surfaces 8a and 9a or 8b and 9b can be at least partially serrated. A final embodiment of either or both of the cooperating surfaces can be an elliptical or egg shaped configuration, e.g. as described in U.S. design patent application Ser. No. 392,181, filed June 28, 1982, which is incorporated herein by reference.

Figure 8:
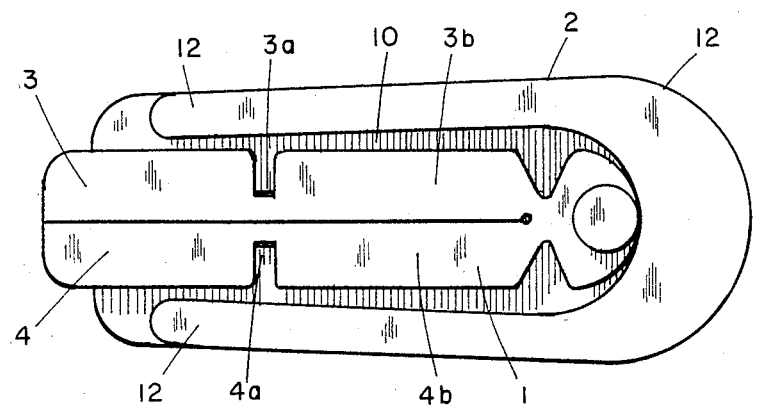
FIG. 8 is a side view and FIG. 11 is a perspective view showing the clip of FIGS. 1 to 4 and the U-shaped member of FIGS. 5 to 7 in a closed configuration.

Referring to FIGS. 1, 5 to 8 and 10, part 2 comprises a means 10 and 11 for approximating the cooperating surfaces 8a and 9a of the two arms 3 and 4, and 8b and 9b of the two nonparallel members 3b and 4b. As specifically shown in FIGS. 5 to 8, part 2 comprises an essentially U-shaped member. In FIG. 8 (see also FIG. 11), each of the two legs 10 and 11 is essentially less than the length of the respective track 15 and 16. It is to be understood, however, that alternatively the two legs 10 and 11 can be essentially equal to the length of the respective tracks 15 and 16.

Reinforcing ribs 12 and 13 can be placed on either or both sides of the legs 10 and 11, and also (e.g., as shown with reinforcing rib 12) on the apex 14 of the U-shaped member. The reinforcing ribs tend to decrease, if not eliminate, the possible twisting motion of the legs 10 and 11 after the arms 3 and 4 and nonparallel members 3b and 4b are approximated, as shown in FIGS. 8 and 11.

Figure 2:
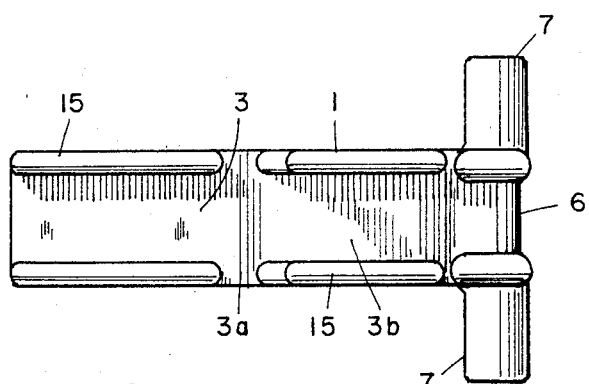
Figure 4:
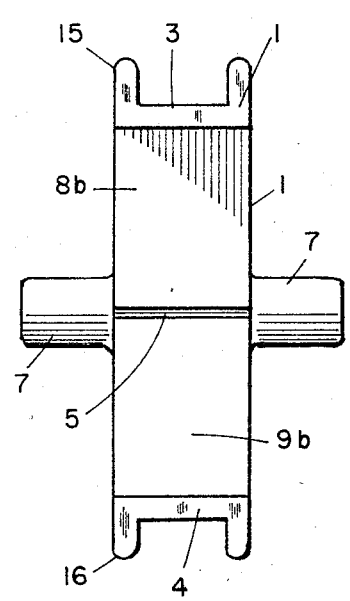
Figure 6:
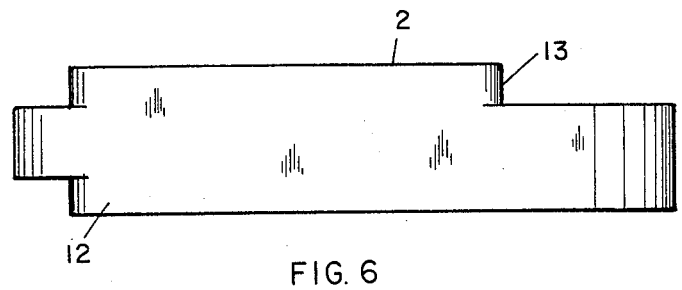
FIGS. 5 to 7 are side, top and front views, respectively, of a U-shaped member which is useful as a means for approximating the cooperating surfaces of the clip shown in FIGS. 1 to 4.
Figure 7:
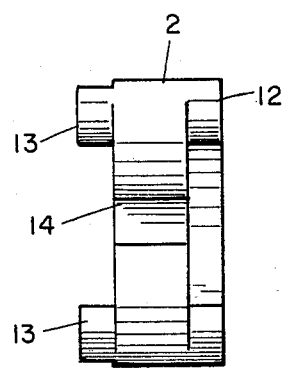
Figure 5:
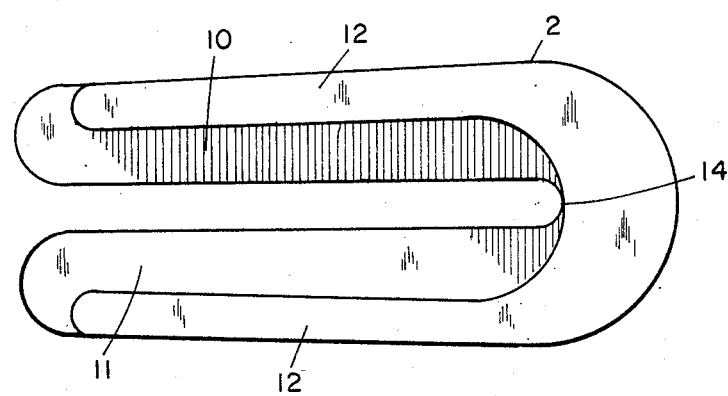
Figure 10:
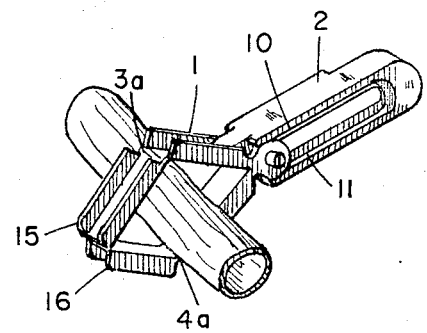
FIG. 10 is a perspective view of the clip of FIG. 9 in a partially closed configuration, showing a diamond-shaped enclosure about a tubular vessel.

Referring to FIGS. 1, 2, 8, 10 and 11, critical to the practice of this invention are the weakened portions 3a and 4a. In FIG. 1, the weakened portions 3a and 4a are shown as openings in the tracks 15 and 16. However, it is to be understood that the weakened portions can be manufactured by other means, e.g. but not limited to, one or more perforations, or one or more continuous or discontinuous indentations or deformations. An example of two continuous indentations are shown in FIG. 2 as double score lines adjacent to the weakened portion 3a. The perforation(s), indentation(s) or deformation(s) can be used either alone or in combination with each other, or in combination with the weakened portions 3a and 4a as shown in FIGS. 1 and 10.

Figure 11:
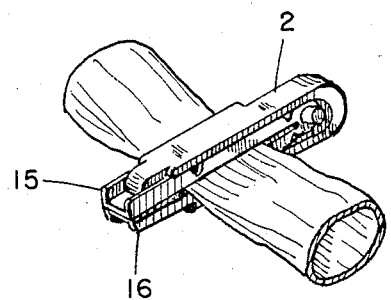

To obtain the same configuration of part 1 shown in FIGS. 10 and 11, the perforation(s), indentation(s) or deformation(s) must be in essentially the same area as the weakened portions 3a and 4a.

It is to be understood that weakened portions 3a and 4a are relatively weaker than the cooperating surfaces 8a, 8b, 9a and 9b but rigid enough to maintain the shape of part 1 of the clip, e.g. as shown in FIG. 9, until a force is applied by the U-shaped part 2. This combination of adequate rigidity of the clip part 1 in its non-crimped configuration and of the ability of the clip part 1 to preselectively begin to crimp at the weakened portions 3a and 4a enables the surgical ligating clip of this invention to ligate a tubular structure in the same manner as a metallic clip. That is, as shown in FIG. 9, the clip is placed around the blood vessel, in FIG. 10 the tips of part 1 touch each other to form a diamond shaped enclosure around the tubular structure, and in FIG. 11 the arms 3 and 4 and the members 3b and 4b are approximated.

Referring again to FIGS. 1 to 4, the means 6 for holding the part 1 in a contiguous relationship with the distal end of the part 2 can further comprise one or more tabs 7. Either the protrusion 6 and/or the tabs 7 are movably contained by a mechanical applicator (see e.g., FIG. 9). The means for containing the protrusion 6 and/or the tabs 7 at the distal end of the mechanical applicator are known in the prior art and can be, e.g., a notch at the distal end of the applicator. After the clip is in an approximated position, as shown e.g. in FIG. 11, the protrusion 6 and/or the tabs 7 can separate from the notch, e.g. by a manual force transmitted to the distal end of the applicator.

The type of mechanical applicator useful in movably containing the ligating clip is not critical to the practice of this invention. That is, an applicator from the prior art can be used to apply the ligating clip to a living mammalian tissue, e.g. an artery. Examples of prior art applicators which can be used include, but are not limited to, a push-pull type, such as a plunger or piston device, and a fulcrum type, such as a medical device having scissors-like or pliers-like handles.

Referring to FIGS. 9 to 11, a push-pull applicator (such as a plunger device) can be used by pushing down on the plunger 17, for example with the thumb. This causes the legs 10 and 11 of part 2 to be engaged between the respective tracks 15 and 16 of the other part 1. Partially pushing down on the plunger effects the diamond-shape configuration of part 1 of the clip, as shown in FIG. 10. Pushing down on the plunger for the complete stroke effects approximation of the tissue between the respective cooperating surfaces 8a and 9a, and 8b and 9b, as shown in FIG. 11.

What is claimed:

1. A nonmetallic surgical clip having two separate parts, the first part comprising two arms joined together at an apex, a pair of tracks contained on the opposite exterior surface of each arm, a weakened portion and a bend in at least one arm, said bend being at said weakened portion and the amount of said bend being such that at least a part of one arm is in an essentially parallel relationship with at least a part of the other arm, and the second part comprising a U-shaped member having two legs capable of being engaged between the respective tracks of said first part for approximating the cooperating surfaces of said arms.

2. A nonmetallic synthetic bioabsorbably surgical clip having two separate parts, the first part comprising two symmetrical arms joined together at an apex, a protrusion adjacent said apex and opposite the proximal ends of said arms, a weakened portion and a bend in each arm, said bend being at said weakened portion and the amount of said bend being such that the distal ends of said arms are in an essentially parallel relationship, and the second part comprising a U-shaped member for approximating the cooperating surfaces of said arms, wherein the distal end of said U-shaped member is contacting said protrusion.

3. A clip of claim 1 or 2 wherein the nonmetallic material is a synthetic bioabsorbable polymer having a glycolic acid ester linkage.

4. A clip of claim 3 wherein said first part is a copolymer containing glycolic acid ester and trimethylene carbonate linkages, and said second part is a homopolymer of glycolic acid.

5. A clip of claim 1 wherein the apex of said first part is essentially contiguous with a portion of said second part.

* * * * *